United States Patent

Minoz

[11] Patent Number: 6,128,520
[45] Date of Patent: Oct. 3, 2000

[54] AMBULATORY RECORDER HAVING VOLATILE AND NON-VOLATILE MEMORIES

[75] Inventor: Alain Minoz, Bromma, Sweden

[73] Assignee: Medtronic, Inc., Minneapolis, Minn.

[21] Appl. No.: 09/130,150

[22] Filed: Aug. 6, 1998

[51] Int. Cl.[7] ..................................................... A61B 5/00
[52] U.S. Cl. ........................ 600/361; 600/300; 600/508
[58] Field of Search ..................................... 600/300, 301, 600/309, 361, 508, 509; 128/920, 521, 503

[56] References Cited

U.S. PATENT DOCUMENTS

| | | |
|---|---|---|
| D. 396,037 | 7/1998 | Cappa et al. . |
| 3,898,984 | 8/1975 | Mandel et al. . |
| 3,941,137 | 3/1976 | Vredenbregt et al. . |
| 4,003,379 | 1/1977 | Ellinwood, Jr. . |
| 4,082,084 | 4/1978 | Lipscher . |
| 4,129,125 | 12/1978 | Lester et al. . |
| 4,183,354 | 1/1980 | Sibley et al. . |
| 4,198,963 | 4/1980 | Barkalow et al. . |
| 4,333,475 | 6/1982 | Moreno et al. . |
| 4,353,375 | 10/1982 | Colburn et al. . |
| 4,365,636 | 12/1982 | Barker . |
| 4,370,983 | 2/1983 | Lichtenstein . |
| 4,464,172 | 8/1984 | Lichtenstein . |
| 4,503,859 | 3/1985 | Petty et al. . |
| 4,529,401 | 7/1985 | Leslie et al. . |
| 4,531,527 | 7/1985 | Reinhold, Jr. et al. . |
| 4,592,018 | 5/1986 | Wiegman . |
| 4,628,928 | 12/1986 | Lowell . |
| 4,632,119 | 12/1986 | Reichstein . |
| 4,667,682 | 5/1987 | Ihlenfeld, III . |
| 4,684,367 | 8/1987 | Schaffer et al. . |
| 4,715,385 | 12/1987 | Cudahy et al. . |
| 4,748,562 | 5/1988 | Miller et al. . |
| 4,771,772 | 9/1988 | DeWitt . |
| 4,774,956 | 10/1988 | Kruse et al. . |
| 4,794,934 | 1/1989 | Motoyama et al. . |
| 4,895,161 | 1/1990 | Cudahy et al. . |
| 4,900,305 | 2/1990 | Smith et al. . |
| 4,917,092 | 4/1990 | Todd et al. . |
| 4,974,599 | 12/1990 | Suzuki . |
| 5,002,062 | 3/1991 | Suzuki . |
| 5,007,427 | 4/1991 | Suzuki et al. . |
| 5,010,888 | 4/1991 | Jadvar et al. . |
| 5,012,411 | 4/1991 | Policastro et al. . |
| 5,016,636 | 5/1991 | Kulakowski . |
| 5,042,481 | 8/1991 | Suzuiki et al. . |
| 5,072,458 | 12/1991 | Suzuki . |
| 5,086,778 | 2/1992 | Mueller et al. . |
| 5,107,835 | 4/1992 | Thomas . |
| 5,111,396 | 5/1992 | Mills et al. . |
| 5,111,818 | 5/1992 | Suzuki et al. . |
| 5,113,869 | 5/1992 | Nappholz et al. . |
| 5,117,827 | 6/1992 | Stuebe et al. . |
| 5,131,816 | 7/1992 | Brown et al. . |
| 5,158,083 | 10/1992 | Sacristan et al. . |
| 5,188,104 | 2/1993 | Wernicke et al. . |
| 5,213,568 | 5/1993 | Lattin et al. . |
| 5,222,503 | 6/1993 | Ives et al. . |
| 5,224,485 | 7/1993 | Powers et al. . |
| 5,226,431 | 7/1993 | Bible et al. . |
| 5,228,450 | 7/1993 | Sellers . |

(List continued on next page.)

FOREIGN PATENT DOCUMENTS 0 356 603   9/1988   Sweden .

*Primary Examiner*—Eric F. Winakur
*Attorney, Agent, or Firm*—Thomas F. Woods; Michael J. Jaro; Harold Patton

[57] ABSTRACT

An ambulatory recorder having a volatile and a non-volatile memory is described. The recorder actively manages the transfer of the data in the volatile to the non-volatile memory. In particular, the sampling frequency and number of channels to be sampled are monitored. These parameters, along with the total buffer size available, are used to determine the final complete data set which can be stored in the buffer. Thereafter, the contents of the buffer are transferred to the non-volatile memory. In such a manner the recorder avoids filling the buffer in the middle of a sampling tick, in which case the remaining data to be sampled would be lost.

24 Claims, 7 Drawing Sheets

U.S. PATENT DOCUMENTS

| | | |
|---|---|---|
| 5,238,001 | 8/1993 | Gallant et al. . |
| 5,261,401 | 11/1993 | Baker et al. . |
| 5,263,491 | 11/1993 | Thornton . |
| 5,273,033 | 12/1993 | Hoffman . |
| 5,292,344 | 3/1994 | Douglas . |
| 5,305,202 | 4/1994 | Gallant et al. . |
| 5,305,761 | 4/1994 | Byrne et al. . |
| 5,307,263 | 4/1994 | Brown . |
| 5,309,920 | 5/1994 | Gallant et al. . |
| 5,338,157 | 8/1994 | Blomquist . |
| 5,341,291 | 8/1994 | Roizen et al. . |
| 5,343,870 | 9/1994 | Gallant et al. . |
| 5,355,892 | 10/1994 | Saltzstein . |
| 5,368,562 | 11/1994 | Blomquist et al. . |
| 5,381,351 | 1/1995 | Kwong et al. . |
| 5,388,587 | 2/1995 | Knutsson et al. . |
| 5,411,022 | 5/1995 | McCue et al. . |
| 5,429,602 | 7/1995 | Hauser . |
| 5,431,634 | 7/1995 | Brown . |
| 5,432,698 | 7/1995 | Fujita . |
| 5,438,985 | 8/1995 | Essen-Moller . |
| 5,479,019 | 12/1995 | Gross . |
| 5,479,935 | 1/1996 | Essen-Moller . |
| 5,507,904 | 4/1996 | Fisher et al. . |
| 5,526,809 | 6/1996 | Fiddian-Green . |
| 5,545,183 | 8/1996 | Altman . |
| 5,607,460 | 3/1997 | Kroll . |
| 5,645,068 | 7/1997 | Mezack et al. . |
| 5,657,759 | 8/1997 | Essen-Moller . |
| 5,701,894 | 12/1997 | Cherry et al. . |
| 5,704,368 | 1/1998 | Asano et al. . |
| 5,704,890 | 1/1998 | Bliss et al. . |
| 5,749,907 | 5/1998 | Mann . |

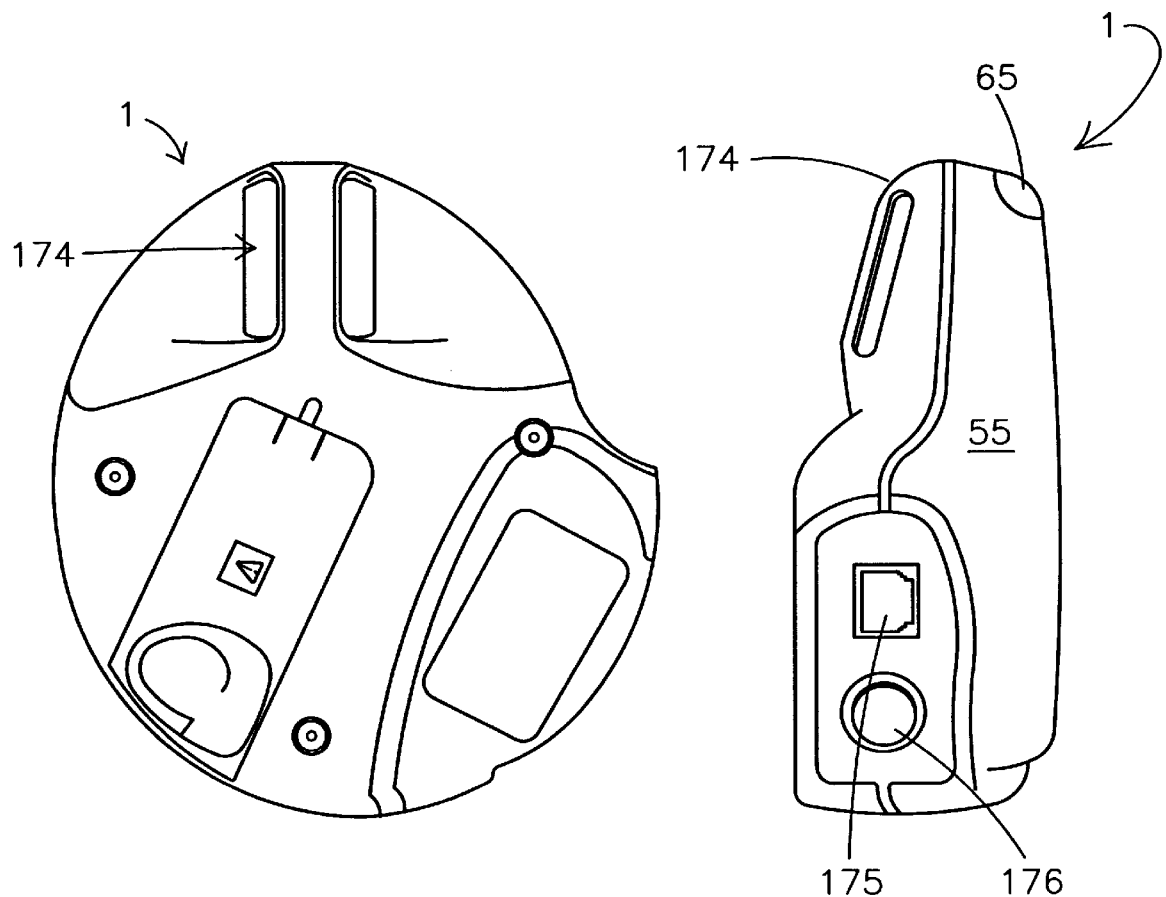
FIG. 6  FIG. 7

AMBULATORY RECORDER HAVING VOLATILE AND NON-VOLATILE MEMORIES

FIELD OF THE INVENTION

The present invention relates to ambulatory recording for medical and especially diagnostic purposes, and particularly to an ambulatory recorder having a volatile and a non-volatile memory.

BACKGROUND OF THE INVENTION

Various physiologic signals are often recorded and analyzed. These signals may included digestive pH, various digestive motility and pressure signals, EEG and EMG, signals, and so on.

Typically, physicians require the concurrent recording a variety of physiologic signals. For example, gastric pH is often collected at the same time as pressure. Through the concurrent collection of various parameters the physician may better understand the patient's condition.

Ambulatory recording and recorders are widely used to collect such data. Such devices include the Digitrapper Mk III™ ambulatory recorder from Synectics Medical AB, the GastroScan II™ from Medical Instruments Corporation, and the SuperLogger™ from Sandhill Scientific. These types of devices make it possible for patients to remain at home, or at least to be ambulant in a hospital setting while physiological data is recorded. Typically the devices comprise a lightweight recorder in which the desired physiological data signals are temporarily stored and later downloaded for future analysis.

Many types of physiological data may be recorded, including ECG (Electrocardiogram) data, EEG (Electroencephalogram) data or pH and pressure data (Motility) in the gastrointestinal tract. Preferably such a recorder should be able to record among a programmable number of channels at a variety of programmable frequencies.

Among the problems with current recorders, however, is that of energy usage. Such recorders, because they must be ambulatory, are battery powered. Thus an ambulatory medical recorder must minimize energy usage while performing almost constant sampling across a variable number of channels at one or more frequencies.

One approach to limit power consumption, while still permitting an enhanced graphical user interface, is to equip the device with two microprocessors. A first, real time processor for sampling, which operates with a relatively low current drain, and a second, non time processor for permitting an enhanced graphical user interface are employed.

Such a device, comprising a real time sampling processor, volatile memory, and a non real time operating system processor, and a non-volatile memory must, however periodically transfer the data collected in the volatile memory to the non-volatile memory.

Typically such a device samples and collects data during specific processor power on or "awake" cycles. One problem which may arise during such data transfer is when the device samples along several channels and the volatile memory becomes filled before all the channels to be sampled at a particular time are actually sampled. That is, if a memory buffer is filled during a tick before all the channels are sampled, then the remaining data which should be collected is not collected and is thus lost.

SUMMARY OF THE INVENTION

An ambulatory recorder having a volatile and a non-volatile memory is described. The recorder actively manages the transfer of the data in the volatile to the non-volatile memory. In particular, the sampling frequency and number of channels to be sampled are monitored. These parameters, along with the total buffer size available, are used to determine the final complete data set which can be stored in the buffer. Thereafter, the contents of the buffer are transferred to the non volatile memory. In such a manner the recorder avoids filling the buffer in the middle of a sampling tick, in which case the remaining data to be sampled would be lost.

BRIEF DESCRIPTION OF THE DRAWINGS

FIG. 6 is a back view of the recorder.

FIG. 7 is a side view of the recorder

The FIGS. are not necessarily to scale.

DETAILED DESCRIPTION OF THE DRAWINGS

Figure 1A:
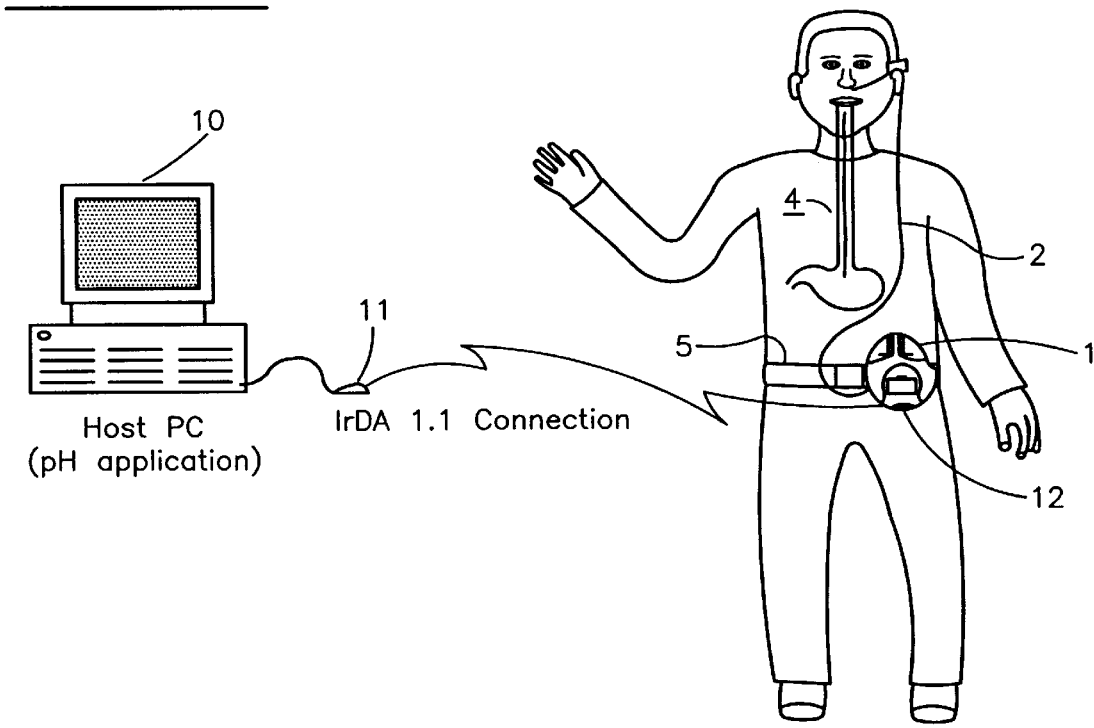
FIG. 1A depicts an ambulatory recorder of the present invention.

FIG. 1A depicts an ambulatory recorder of the present invention. As seen, ambulatory recorder 1 of the present invention may be carried by a patient. In the preferred embodiment, the recorder may be either carried through a mounting in the back of the recorder enclosure which fastens to a patient's belt 5, or the same mounting may be coupled to be carried using a shoulder harness (not shown). As seen, recorder is coupled to the patient 4 through one or more sensing catheters 2. Sensing catheters may be positioned in any area of the patient's body from which data is to be sensed, including the esophagus, as depicted in this FIG. It should be noted that the ambulatory recorder of the present invention may be used to collect many or various types of data including gastrointestinal data such as pH and pressure data, neurological, and neuromuscular, EEG or EMG data.

Among the various sensing catheters which may be coupled to the device are manometry catheters and pH testing catheters, including the Synectics Medical AB, Stockholm, Sweden Model G 91-9 series of Multi use pH catheters; Synectics Medical AB Model G 91-2 series of Multi use pH catheters with perfusion port; or the Zinectics Inc., Salt Lake City, Utah disposable 24 pH catheter Model series G91-6 or G 91-7. While a single catheter 2 is shown depicted in this figure, recorder further permits two separate sensors to be coupled to the device, as seen in FIG. 1B.

As further seen in this figure, the recorder may also communicate with a host PC 10 via an infra red data link facility through an IrDA connection 11, such as, a JETEYE ESI-57680 device available from Extended Systems, Inc., Boise, Id., which communicates with the recorder using the infra Red Data Association 1.1 Connection Protocol. As seen, infra red data connection establishes a communication link to infra red port 12 on recorder 1.

Figure 1B:
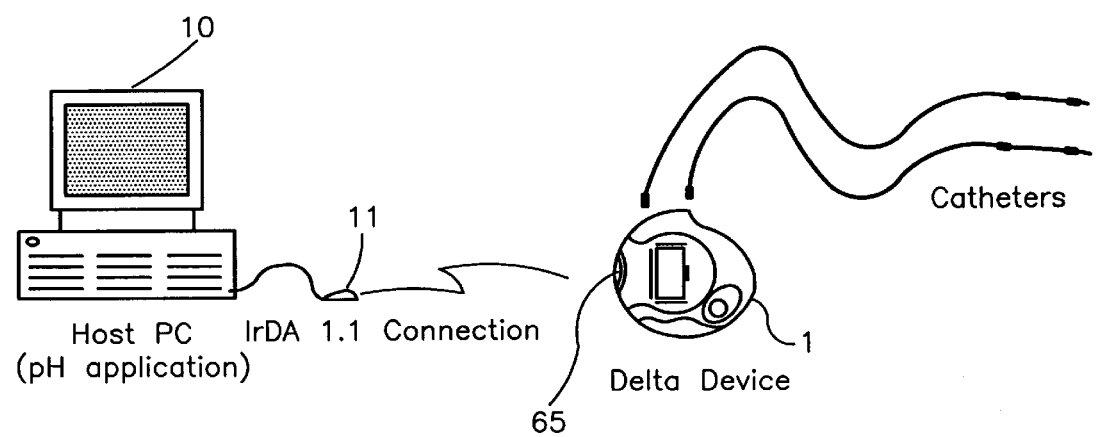
FIG. 1B illustrates a further manner in which the recorder 1 may also establish an infra red data communication link with a host PC.

FIG. 1B illustrates a further manner in which the recorder 1 may also establish an infra red data communication link with a host PC. In particular, the infra red data communication data recorder may be established when the recorder is not worn by the patient. As discussed in more detail below, one of the advantages of the present invention is that the infra red data components and recorder case permit such a link to be established when the device is worn as shown in FIG. 1A or when the device is removed from the patient and positioned in proximity to mouse 11.

Figure 2:
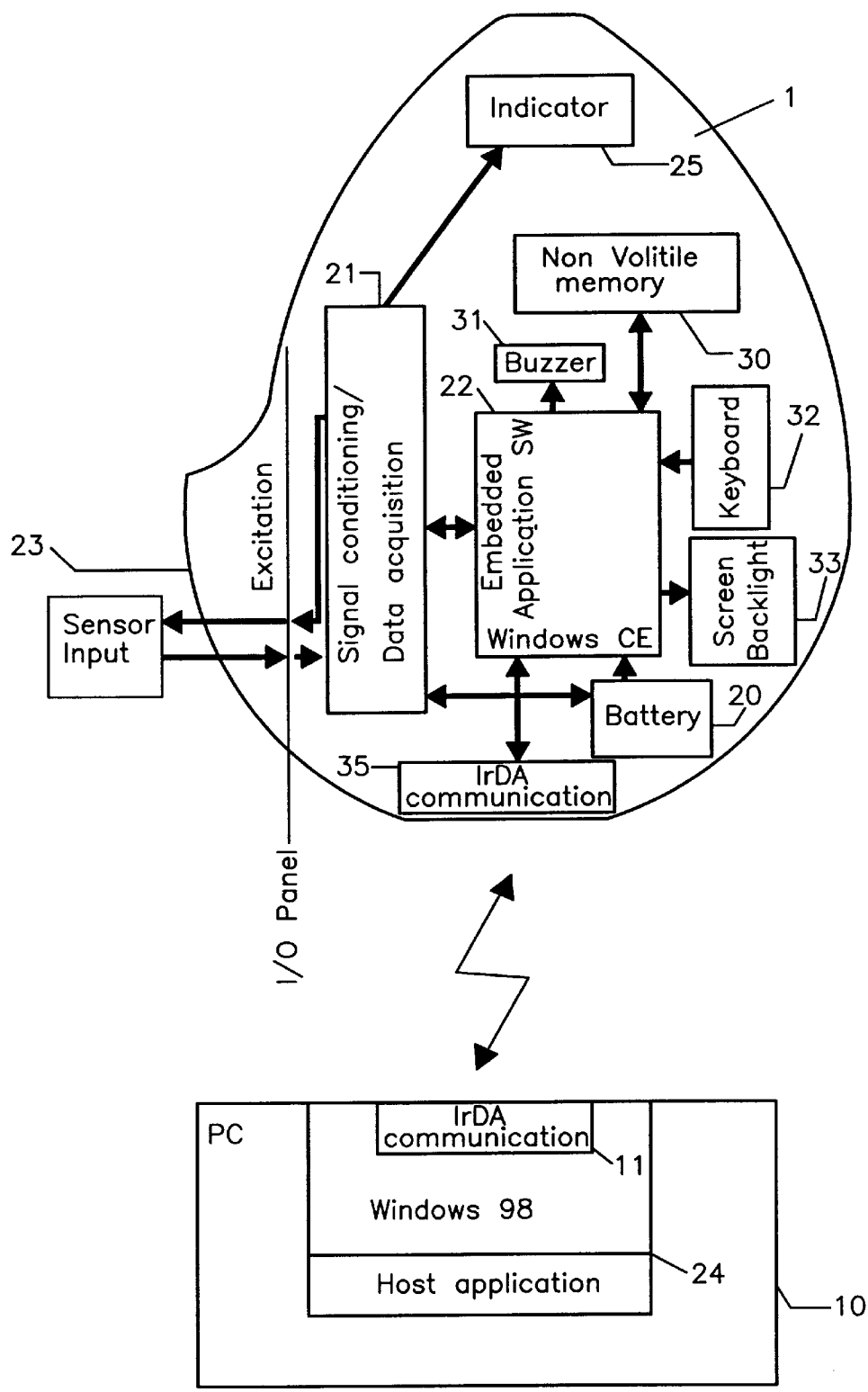
FIG. 2 is a block diagram of the data recording system shown in FIG. 1B.

FIG. 2 is a block diagram of the data recording system shown in FIG. 1B. As seen, recorder 1 features a battery 20 which is coupled to the signal conditioning/data acquisition block driven by a real time processor 21. Battery 20 powers non-real time processor 22 that runs the application. As disclosed in more detail below, real time processor 21 is a low power processor which is used to sample data which is received from sensor input 23 by a sensor attached thereto (not shown in FIG. 2).

Sampling is achieved through the signal conditioning providing an excitation to the sensor coupled to sensor input 23. Such excitation voltage is often used to power and, thus, permit sensing to occur in a variety of different types of sensors, including pressure sensors, as is well known in the art. The sampling and sensing controls are provided by the real time processor 21. Real time processor also drives a LED indicator 25 to show the system is running even when the screen is off.

As further seen, this processor is coupled to second non-real time processor 22. Second processor 22 is provided primarily to perform those high processing operations associated with multitasking, graphical user interface, floating point calculation, Infra Red communication and long term memory storage. In particular, second processor is primarily provided to operate a Windows CE operating system as well as one or more embedded applications, as depicted. As further seen, this processor is coupled to audible buzzer 31 as well as keyboard controls 32, a screen 33 and non-volatile memory 30. Non-volatile memory provides a long term memory for the device such that data can be recorded and preserved, even if power is lost. In the preferred embodiment, keyboard controls processes a series of four push buttons, each of which provide one or more different types of system inputs, as provided by the Windows CE™ operating system, available from Microsoft Corporation, Redmond, Wash.

As further seen in this figure, recorder features an infra red port 35 to communicate with the host PC. As depicted in FIG. 1B, the infra red connection permits recorder 1 to receive and exchange data with host PC 10. Host PC, as seen, includes both a Windows 98™ operating system available from Microsoft Corporation, Redmond, Wash., as well as one or more host applications. Host applications permit the diagnosis of the recorded values.

In a preferred embodiment of the present invention, the real time processor 21 is a model PIC16LC67 IC from Microchip Technology Inc., Chandler, Ariz.; non-real time processor 22 is a model ElanSC400 IC from Advanced Micro Devices, Inc. Sunnyvale, Calif.; and non-volatile memory 30a is the model Minicard AMMCL004AWP from Advanced Micro Devices, Inc. Sunnyvale, Calif.

As discussed above, the recorder of the present invention operates by sampling data from real time processor 21. Real time processor 21 includes a buffer memory such as a volatile memory, or such as RAM which temporarily stores the sampled data sets collected during each microprocessor wake-up or tick cycle. Prior to the memory being filled, however, it is important that the memory buffer contents be transferred to non-volatile permanent memory for further future access and analysis.

Because the number of channels which are sampled as well as the frequencies at which each of these channels are sampled may be programmed, there are possible variations between the sizes of the data points collected during each processor wake-up cycle. As mentioned above, one of the problems which may occur is, prior to the memory buffer having its contents transferred to the non-volatile memory, the buffer itself can be filled within a processor wake-up cycle. At this point the remaining data to be sampled could be lost.

The present invention solves this problem by monitoring the memory size of the buffer along with the amount of samples to be collected during each specific tick or a sample cycle. In such a manner, the present invention permits the recorder to transfer and manage the memory buffer size such that there will always be room for the complete set of data samples scheduled to be collected during the next tick or sample cycle.

Figure 3A:
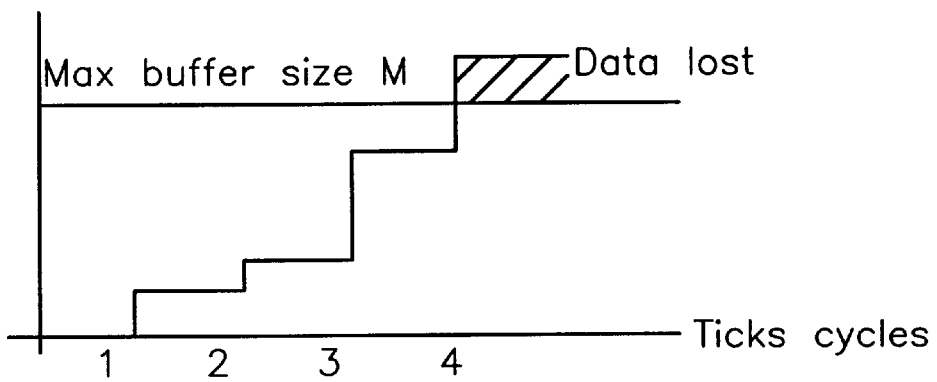
FIG. 3A illustrates a buffer being filled in the middle of a tick.

FIG. 3A illustrates a buffer being filled in the middle of a tick or sample cycle. As seen, memory has a maximum buffer size M. At tick 1 memory buffer has an amount of data stored into it. Equal amounts of data are stored during ticks 2 and 3. (Note, in this example, an unequal amount of data is collected at each tick, because of different sampling rates being employed although as can be appreciated equal amounts of data can be collected over various cycles in some cases). As seen, at tick 4, the memory had less capacity than the amount of data which was collected during the tick, i.e. the maximum buffer size M was exceeded prior to the full amount of data being collected during tick 4. As illustrated, this resulted in data being lost, i.e. not stored in the memory and, thus, not able to be stored in the non-volatile permanent memory for further analysis.

Figure 3B:
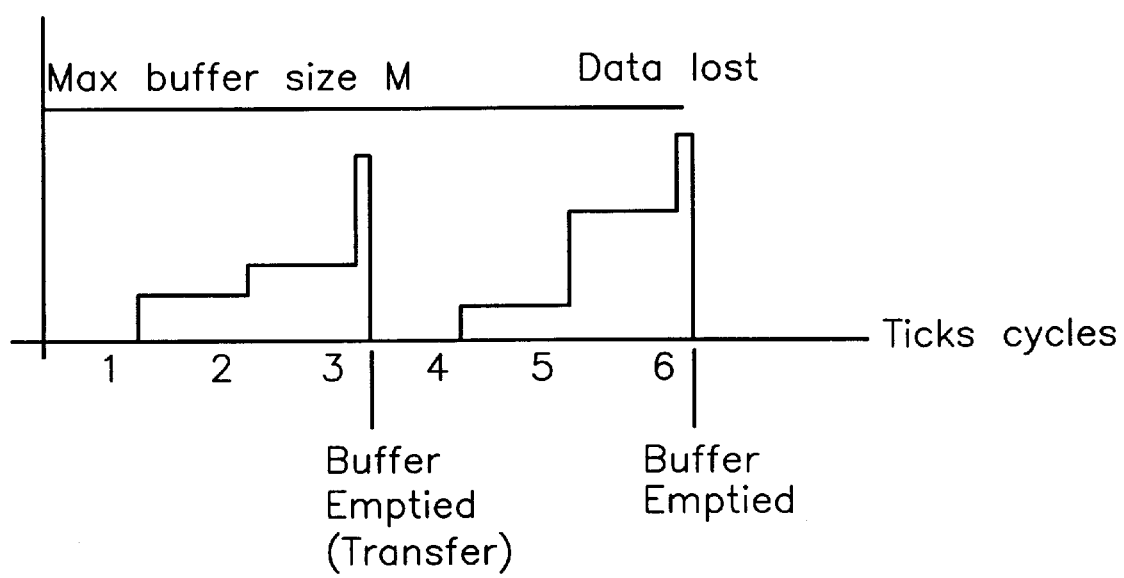
FIG. 3B further illustrates how to avoid the overflow.

FIG. 3B further illustrates how to avoid the overflow: The real time processor needs to download its buffer after a completed sampling every 3 ticks. The buffer is therefore emptied before reaching its limit. The principle is to calculate the maximum number of ticks to complete before emptying the buffer that will assure that the buffer is never overflowed according to how many channels the device samples and according to the different frequencies. The number of maximum ticks is calculated before sampling is initiated and is used during the entire recording period. The advantage of calculating only once and not on the fly after each tick is that the microprocessor uses fewer computation cycles and therefore less energy.

Figure 3C:
FIG. 3C further illustrates the memory filling and availability during each processor wake-up cycle or tick.

FIG. 3C further illustrates the memory filling and availability during each processor wake-up cycle or tick. The reader should note the sampling channels and frequencies used in this illustration do not correspond with those used in FIGS. 3A and 3B, discussed above. As seen at tick 1, the processor samples along channels 1 and 2. At the beginning of the wake-up cycle no samples are stored in the memory and twelve spaces are available. After the tick is completed, two samples are stored in volatile memory and ten remaining spaces are available. During tick 2 sampling occurs along channels 1 and 4. During this tick two additional samples are collected and the number of samples in the volatile memory increases from two, at the beginning of the wake-up cycle, to four, at the end of the wake-up cycle. Concomitantly, the number of spaces available in the volatile memory decreases from ten, at the beginning of the wake-up cycle, to eight, at the end of the wake-up cycle. A continual increase in the number of samples in the volatile memory occurs through ticks 3, 4 and 5 with a concomitant decrease in the number of spaces available in the volatile memory, until, as seen, at the end of tick 5, the number of spaces available in volatile memory at the end of the wake-up cycle is one. As seen, this causes data loss during tick 6 (i.e., during tick 6 data from channels 1, 2 and 3 are lost). As seen, however, the number of samples in the volatile memory at the beginning of the wake-up cycle is eleven and only one space is available in the volatile memory at the beginning of the wake-up cycle. Thus, during tick 6 there is not enough space in the volatile memory to store all the samples which are desired. At this point, a memory overfill would be seen and some or all of the data to be collected in tick 6 would be lost.

Figure 4:
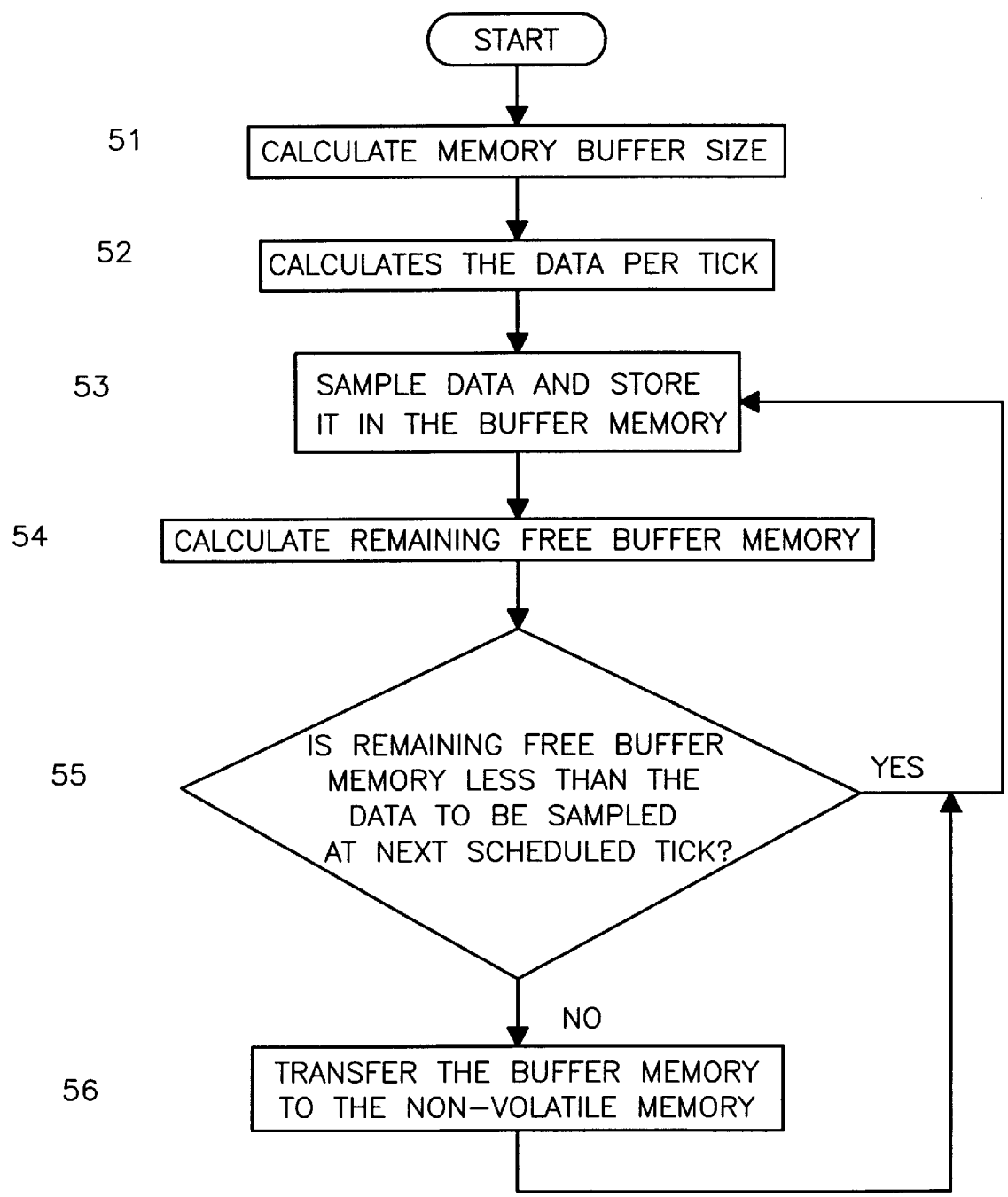
FIG. 4 depicts the general steps used to manage the memory buffer size such that there will always be room for the complete set of data samples scheduled to be collected during the next tick cycle.

FIG. 4 depicts the general steps used to manage the memory buffer size such that there will always be room for the complete set of data samples scheduled to be collected during the next tick cycle. As seen in step 51, the memory buffer size is calculated. Next, the recorder proceeds to block 52 and calculates the data per tick Next, the recorder proceeds to block 53 and samples data and stores it in the buffer memory. In block 54 the remaining free buffer memory is calculated. Next, at 55 a decision is made whether the remaining free buffer memory is less than the data before next scheduled tick. If it is, the recorder proceeds back to block 53 and samples the data and puts it in the memory. If, however, the remaining free buffer memory is less than the size of the data set before next scheduled tick, the recorder would proceed to block 56 and transfer the buffer memory to the non-volatile memory prior to again returning to block 53. In such a manner, the recorder is able to manage the buffer memory size so that there is always enough remaining free buffer memory to permit the next data set to be stored.

Figure 5:
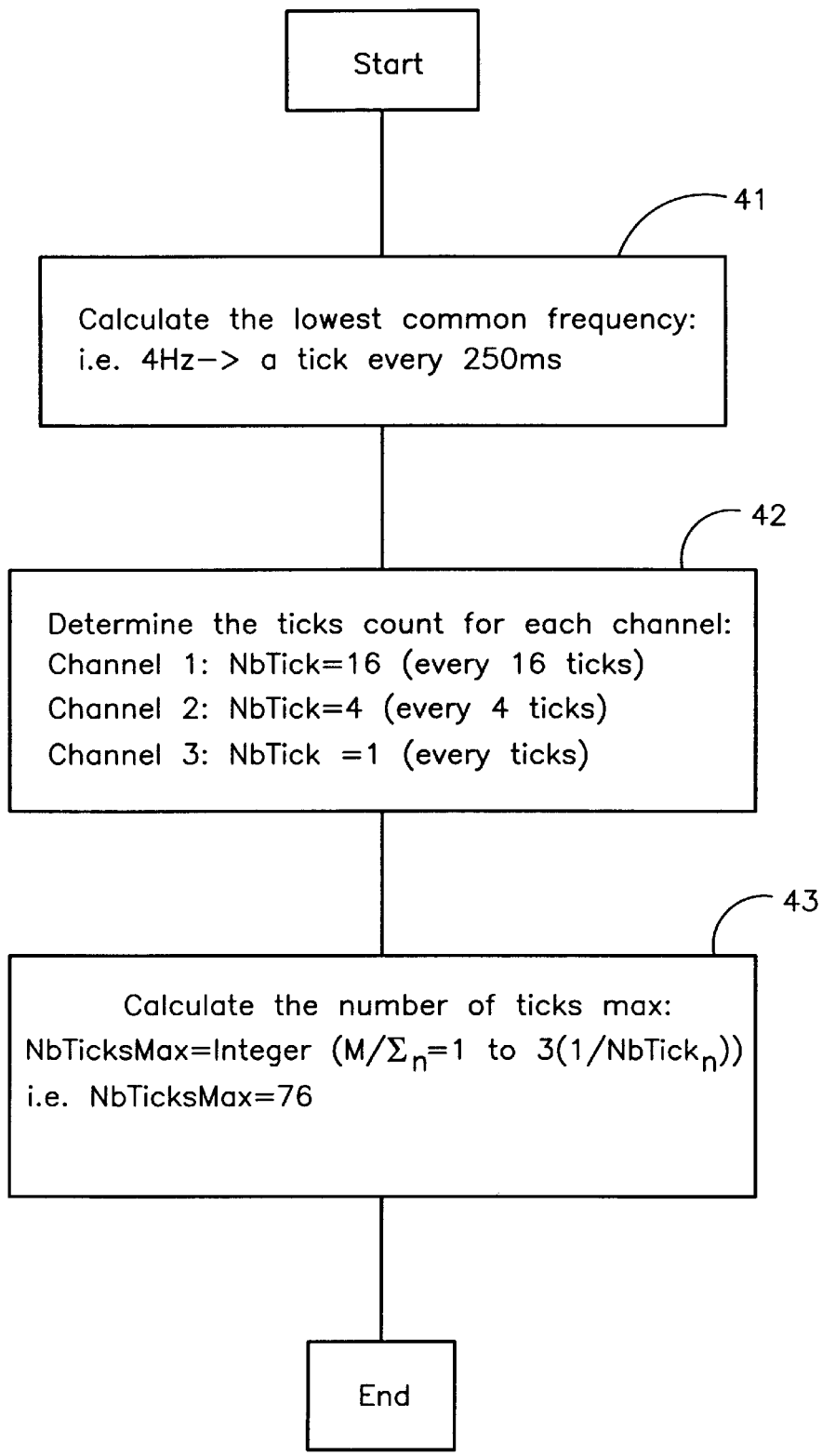
FIG. 5 illustrates how to calculate the number of tick max per buffer.

FIG. 5 illustrates how to calculate the number of maximum ticks per buffer. The initial condition is that every channel has been assigned a sampling frequency. For example, we can take 3 channels with channel 1 at ¼ Hz, channel 2 at 1 Hz and channel 3 at 4 Hz. At 41, the device examines the frequencies at which sampling is to occur for every channel and calculates the lowest common frequency (4 Hz in our example). Next, at 42 the device sets or determinates respective tick count for each individual frequency. The tick count represents the number of ticks to wait before sampling a channel. A value of 1 means that a channel is to be sampled every tick, a value of 2 means a channel is sampled every 2 ticks, and so on. In our example, tick count (Nb Tick) n for channel 1 is 16, for channel 2 is 4 and for channel 3 is 1.

Step 43 calculates the Number of Ticks to fill the buffer (NbTicksMax) by:

$$NbTicksMax = M / \Sigma_{n=1 \text{ to } 3}(1/NbTick_n),$$

where

M represents the maximum number of samples that the buffer can contain. In our example, we let M equal to 100, thus producing.

$$\Sigma_{n=1 \text{ to } 3}(1/NTick_n) = 1/16 + 1/4 + 1 = 1.3125,$$

and thus

NbTicksMax=100/1.3125=n6.19

The device truncates this value and thus only takes the integer part (76) to be sure we will never download during a tick and the buffer will never overflow.

FIG. 6 is a back view of the recorder. As seen, recorder 1 features a belt loop 174 which may be used to mount the recorder to a patient using either the patient's belt or the shoulder strap.

FIG. 7 is a side view of recorder 1. As further seen in this view, housing 155 features a pair of sensor inputs 175 and 176. In the preferred embodiment, input 175 is for a pH catheter while input 176 is for a pressure measuring catheter.

What is claimed is:

1. An ambulatory recorder, comprising:

a sensor for sensing at least one physiologic parameter from a patient;

a first real-time processor to perform at least a first process on the at least one physiologic parameter and create a first data set, the first processor further comprising a first volatile buffer memory being suitable to store the first data set, the first volatile buffer memory having a memory limit;

a second non-real time processor to perform at least a second process on the first data set to yield a second data set, the first processor being coupled to the second processor so that the first data set may be transferred to the second processor from the first processor;

a second non-volatile memory coupled to the second processor, the second memory being suitable for storing the second data set; and means for managing the amount of data stored in the first volatile buffer memory so that the first volatile buffer memory limit cannot be reached.

2. An ambulatory recorder according to claim 1, further comprising means for calculating the volatile memory buffer size limit.

3. An ambulatory recorder according to claim 1, further comprising means for calculating an amount of remaining free volatile buffer memory.

4. An ambulatory recorder according to claim 3, further comprising means for determining whether the amount of remaining free volatile buffer memory is less than the amount of data to be sampled during a subsequent sample cycle.

5. An ambulatory recorder according to claim 4, further comprising means for transferring the first data set from the volatile buffer memory to the non-volatile memory.

6. An ambulatory recorder according to claim 1, further comprising means for mounting the ambulatory recorder to a patient, the mounting means being connected to the recorder.

7. An ambulatory recorder according to claim 6, wherein the mounting means comprises a loop configured for a belt or a shoulder strap to be inserted therethrough.

8. An ambulatory recorder according to claim 1, wherein the sensor comprises a pH sensing catheter.

9. An ambulatory recorder comprising:

a sensor for sensing at least one physiologic parameter from a patient;

a first processor to perform at least a first process on the at least one physiologic parameter and create a first data set, the processor performing the first process during each sample cycle of the processor, the first processor further comprising a first volatile buffer memory suitable for storing the first data set, the first volatile buffer memory having a size limit;

means for calculating the amount of data acquired per sample cycle;

a second non-real time processor to perform at least a second process on the first data set to yield a second data set, the first processor being coupled to the second processor so that the first data set may be transferred to the second processor from the first processor;

a second non-volatile memory coupled to the second processor, the second memory being suitable for storing the second data set; and means for managing the amount of data stored in the first volatile buffer memory so that the first volatile buffer memory limit cannot be reached.

10. An ambulatory recorder according to claim 9, further comprising means for calculating the volatile memory buffer size limit.

11. An ambulatory recorder according to claim 9, further comprising means for calculating an amount of remaining free volatile buffer memory.

12. An ambulatory recorder according to claim 11, further comprising means for determining whether the amount of remaining free volatile buffer memory is less than the amount of data to be sampled during a subsequent sample cycle.

13. An ambulatory recorder according to claim 9, further comprising means for transferring the first data set from the volatile buffer memory to the non-volatile memory.

14. An ambulatory recorder according to claim 9, further comprising means for mounting the ambulatory recorder to a patient, the mounting means being attached to the recorder.

15. An ambulatory recorder according to claim 14, wherein the mounting means comprises a loop configured for a belt or a shoulder strap to be inserted therethrough.

16. An ambulatory recorder according to claim 9, wherein the sensor comprises a pH sensing catheter.

17. A method of operating an ambulatory recorder, the ambulatory recorder comprising at least one sensor for sensing at least one physiologic parameter from a patient, a first real-time processor to perform at least a first process on the at least one physiologic parameter and create a first data set, the first processor further comprising a first volatile buffer memory suitable for storing the first data set, the first volatile buffer memory having a memory limit, a second non-real time processor to perform at least a second process physiologic on the first data set to yield a second data set, the first processor being coupled to the second processor so that the first data set may be transferred to the second processor from the first processor, a second non-volatile memory coupled to the second processor, the second memory being suitable for storing the second data set, and means for managing the amount of data stored in the first volatile buffer memory so that the first volatile buffer memory limit cannot be reached, comprising:

providing the at least one sensor;

providing the first and second processors;

providing the first memory and the second memory;

operatively connecting the sensor, the first and second processors and the first and second memories;

calculating the amount of data acquired per sample cycle.

18. A method of operating an ambulatory recorder according to claim 17, further comprising calculating the first volatile memory buffer size limit.

19. An ambulatory recorder according to claim 18, further comprising sampling medical data and storing said sampled data in the volatile buffer memory.

20. An ambulatory recorder according to claim 19, further comprising calculating remaining free volatile buffer memory.

21. An ambulatory recorder according to claim 20, further comprising determining whether the amount of remaining free volatile buffer memory is less than the amount of data to be sampled during a subsequent sample cycle.

22. An ambulatory recorder according to claim 21, further comprising transferring the volatile buffer memory to the non-volatile memory.

23. An ambulatory recorder according to claim 17, further comprising mounting the ambulatory recorder to a patient.

24. An ambulatory recorder according to claim 17, wherein providing a sensor comprises providing a pH sensing catheter.

* * * * *